US005792332A

United States Patent [19]

Montecino et al.

[11] Patent Number: 5,792,332
[45] Date of Patent: Aug. 11, 1998

[54] SAFE ELECTROPHORESIS UNIT

[75] Inventors: Allen L. Montecino, Berkeley; Eric G. Coates, San Francisco; Eric R. Hungerman, Danville, all of Calif.

[73] Assignee: Hoefer Pharmacia Biotech, Inc., San Francisco, Calif.

[21] Appl. No.: 685,477

[22] Filed: Jul. 24, 1996

Related U.S. Application Data

[60] Provisional application No. 60/009,021 Dec. 21, 1995.

[51] Int. Cl.[6] .......................... G01N 27/26; G01N 27/447
[52] U.S. Cl. ............................................ 204/618; 204/467
[58] Field of Search ................................. 204/618, 467

[56] References Cited

U.S. PATENT DOCUMENTS

| H576 | 2/1989 | Tezuka | 204/600 |
|---|---|---|---|
| 4,574,040 | 3/1986 | Delony et al. | 204/618 |
| 4,663,015 | 5/1987 | Sleeter et al. | 204/618 |
| 4,773,984 | 9/1988 | Flesher et al. | 204/618 |
| 5,112,470 | 5/1992 | Sylvester | 204/618 |
| 5,207,880 | 5/1993 | Middendorf et al. | 204/618 |

Primary Examiner—Bruce F. Bell
Assistant Examiner—John S. Starsiak, Jr.
Attorney, Agent, or Firm—Limbach & Limbach L.L.P.

[57] ABSTRACT

An electrophoresis apparatus which overcomes the safety problems of the conventional apparatus by including a screen for preventing the operator from contacting the exposed surface of the gel chamber to avoid burns or electric shock. Shock due to contact with buffer solutions is also avoided by use of a power engaging mechanism which prevents the operator from accessing either of the buffer reservoirs when one or both of the buffer solutions are connected to the power source. The power engaging mechanism ensures that it is only possible to connect the buffer solutions to the power source when both reservoir covers are in their closed positions.

18 Claims, 4 Drawing Sheets

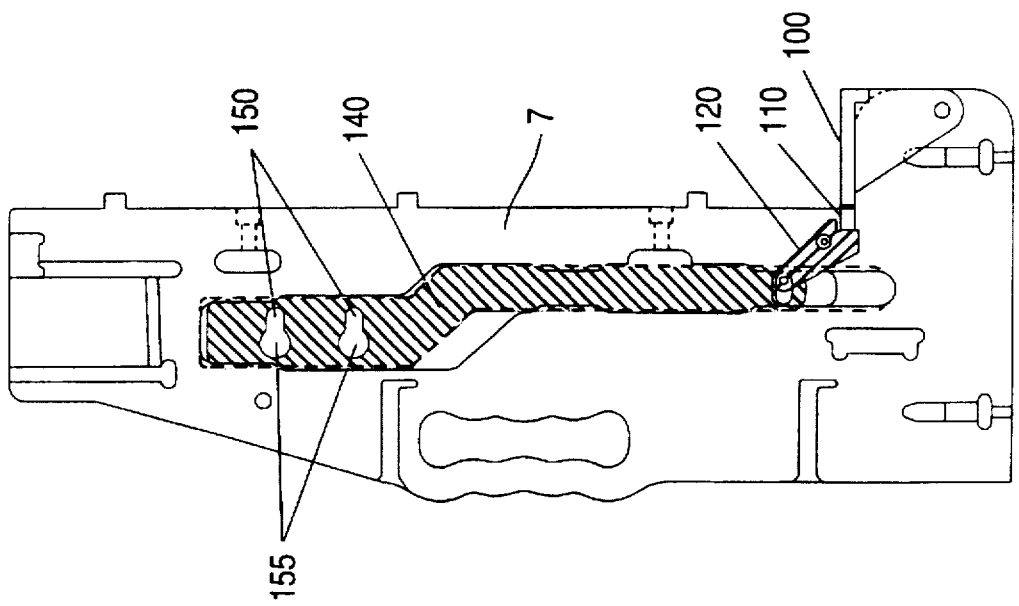
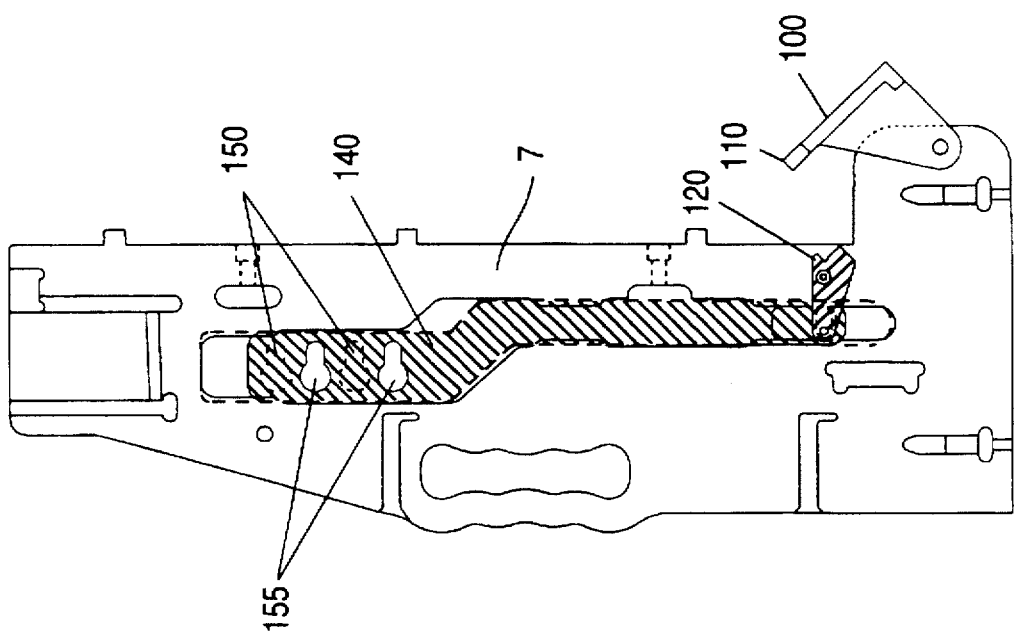

SAFE ELECTROPHORESIS UNIT

This application claims the benefit of U.S. Provisional application Ser. No. 60/009,021, filed Dec. 21, 1995.

BACKGROUND

The present invention relates generally to an electrophoresis apparatus, and more specifically, to an electrophoresis apparatus having safety features for protecting the operator of the unit.

Gel electrophoresis is an important biological assay, in which the constituent components of a sample are separated using the fact that different molecules applied to a gel migrate at different rates when they are subjected to an electric field. This technique has proved very useful in the separation of both DNA and RNA fragments. However, large voltages—up to about 3000 volts—may be required to carry out the separation and this can pose considerable safety hazards to the operator.

In a conventional electrophoresis apparatus the gel itself is contained in a gel chamber that is constructed so that two opposite edges of the gel are exposed. The apparatus further includes two buffer reservoirs for containing buffer solutions. The gel chamber and the reservoirs are arranged so that the exposed edges of the gel are in contact with the buffer solutions. Prior to operation, the sample to be separated is placed close to one of the exposed edges of the gel. A voltage difference is then applied between the two buffer solutions thereby producing a voltage drop across the gel. The voltage drop produces an electric field which causes the separate components of the sample to migrate through the gel at different rates.

An operator using a conventional electrophoresis apparatus is exposed to at least three serious safety hazards.

The first safety hazard is due to the fact that the voltage difference across the gel may produce considerable heat in the gel and the gel chamber may therefore become hot. This heating can affect the migration of the separating components and can lead to a gel showing the "smile" effect. To overcome this drawback, the conventional apparatus may include a heat distribution plate that contacts the back side of the gel chamber and which more evenly distributes the heat over the chamber. The heat distribution plate, however, does not substantially reduce the temperature in the gel and since the operator has unrestricted access to the front side of the gel chamber he or she is therefore exposed to the danger of being burned by the hot gel chamber.

The second safety hazard also concerns operator access to the exposed side of the gel chamber. Although the conventional apparatus is designed so that buffer solution cannot generally leak onto the exposed surface of the chamber, leaks do occur. This situation poses an extreme hazard to the operator, since, if a leak has occurred and the operator touches the exposed surface of the chamber during operation of the unit, the operator could receive an electric shock.

The third safety hazard concerns operator access to the buffer solutions during operation of the unit. The conventional apparatus usually includes upper and lower buffer reservoir covers and the safety feature that a buffer solution cannot be connected to the power source unless the corresponding buffer reservoir cover is closed. However, in the conventional apparatus, one of the buffer electrodes can be connected to the power source while the other reservoir cover is open. This can pose a serious safety hazard since current can flow from one of the buffer solution to the other buffer solution via the gel. Therefore, an operator making contact with one of the buffer solutions while the other buffer electrode is connected to the power source can complete the circuit to ground and hence receive an electric shock.

There do exist electrophoresis units which address some of these safety concerns. For example the Hoefer SE 1600 sequencing gel apparatus includes features which address the problem of making contact with one buffer solution while the other buffer solution could be connected to the power supply. However, the complexity of this apparatus makes it expensive and difficult to assemble.

For these reasons, there is a real need for an electrophoresis apparatus with additional safety features, which is also convenient to assemble and less expensive.

SUMMARY

The present invention addresses this need by providing an electrophoresis apparatus which includes two safety features: first, it provides a means for preventing the operator from contacting the exposed surface of the gel chamber, thereby preventing the operator from being burned if the chamber is hot or from receiving an electric shock if the buffer solution has leaked; and second, it provides a means for preventing the operator from accessing either of the buffer reservoirs when one or both of the buffer solutions are connected to the power source, thereby preventing the operator from receiving an electric shock.

More specifically, the present invention provides an electrophoresis apparatus which includes a protective screen for preventing an operator from contacting the gel chamber; and second, a power engaging mechanism which ensures that either both buffer solutions or neither buffer solution is connected to the power source. The power engaging mechanism further ensures that it is only possible to connect the buffer solutions to the power source when both reservoir covers are in their closed positions and that both reservoir covers are retained in their closed positions when the buffer solutions are connected to the power source.

In one embodiment of the present invention there is provided an electrophoresis apparatus for use with a power source that includes the following elements: a chamber for containing a gel; a frame for supporting the chamber; a first buffer reservoir for containing a first buffer solution in contact with a first edge of the gel; a second buffer reservoir for containing a second buffer solution in contact with a second edge of the gel; a protective screen for preventing an operator from contacting the chamber; a first buffer reservoir cover having a closed position in which it prevents the operator from contacting the first buffer solution; a second buffer reservoir cover having a closed position in which it prevents the operator from contacting the second buffer solution; and a power engaging mechanism for connecting either both buffer solutions or neither buffer solution to the power source, the power engaging mechanism connecting both buffer solutions only when both reservoir covers are in their closed positions and retaining both reservoir covers in their closed positions when the buffer solutions are connected to the power source.

The apparatus may optionally include the following features.

First, the protective screen and the chamber may be removably supported by the frame. In this case, the apparatus may further include a clamping means mounted on the frame for clamping the chamber and the protective screen, the clamping means being capable of clamping the chamber only when the protective screen is also clamped, thereby ensuring that the chamber cannot be installed without the protective screen.

Second, the frame may support the chamber in a substantially vertical position with the first edge of the gel above the second edge of the gel. In this case, the apparatus may further include a drain container connected to the first buffer reservoir for draining the first buffer solution only when the buffer solutions are not connected to the power source.

Third, the protective screen may be transparent.

Fourth, the apparatus may further include a first electrode disengageably connected to the power source for electrically contacting the first buffer solution to the power source and a second electrode disengageably connected to the power source for electrically contacting the second buffer solution to the power source. In this case, the closed position of the first buffer reservoir cover prevents the operator from contacting both the first buffer solution and the first electrode and the closed position of the second buffer reservoir cover prevents the operator from contacting the second buffer solution. Furthermore, the power engaging mechanism connects either both electrodes or neither electrode to the power source, the power engaging mechanism connecting both electrodes only when both reservoir covers are in their closed positions and retaining both reservoir covers in their closed positions when the electrodes are connected to the power source.

Fifth, the frame may include sockets that are capable of accepting a power connector plug only when the first buffer reservoir cover is in its closed position. In this case, the power engaging mechanism includes a shutter which is movably supported by the frame. The shutter has openings that are capable of accepting the power connector plug when they are aligned with the sockets in the frame. The openings are aligned with the sockets in the frame only when the shutter is in an open position. Furthermore, the shutter is connected to the second buffer reservoir cover so that the shutter is in its open position only when the second buffer reservoir cover is in its closed position and the second buffer reservoir cover is retained in its closed position when the shutter is in its open position. When the power connector plug is inserted in the aligned sockets and openings it connects both buffer solutions to the power source, it secures the first buffer reservoir cover in its closed position, and it secures the shutter in its open position thereby securing the second buffer reservoir cover in its closed position.

In a second embodiment of the present invention there is provided an apparatus for use with a power source that includes the following elements: a chamber for containing a gel; a frame for supporting the chamber; a first buffer reservoir for containing a first buffer solution in contact with a first edge of the gel; a second buffer reservoir for containing a second buffer solution in contact with a second edge of the gel; and a protective screen for preventing an operator from contacting the chamber.

In a third embodiment of the present invention there is provided an electrophoresis apparatus for use with a power source that includes the following elements: a chamber for containing a gel; a frame for supporting the chamber; a first buffer reservoir for containing a first buffer solution in contact with a first edge of the gel; a second buffer reservoir for containing a second buffer solution in contact with a second edge of the gel; a first buffer reservoir cover having a closed position in which it prevents the operator from contacting the first buffer solution; a second buffer reservoir cover having a closed position in which it prevents the operator from contacting the second buffer solution; and a power engaging mechanism for connecting either both buffer solutions or neither buffer solution to the power source, the power engaging mechanism connecting both buffer solutions only when both reservoir covers are in their closed positions and retaining both reservoir covers in their closed positions when the buffer solutions are connected to the power source.

BRIEF DESCRIPTION OF THE DRAWINGS

The invention will be better understood by reference to the figures, in which:

FIGS. 3A and 3B show side views of the embodiment shown in FIGS. 1 and 2; and

DETAILED DESCRIPTION

An exemplary embodiment of the invention which incorporates the above safety features will now be described in detail, with reference to the figures.

Figure 1:
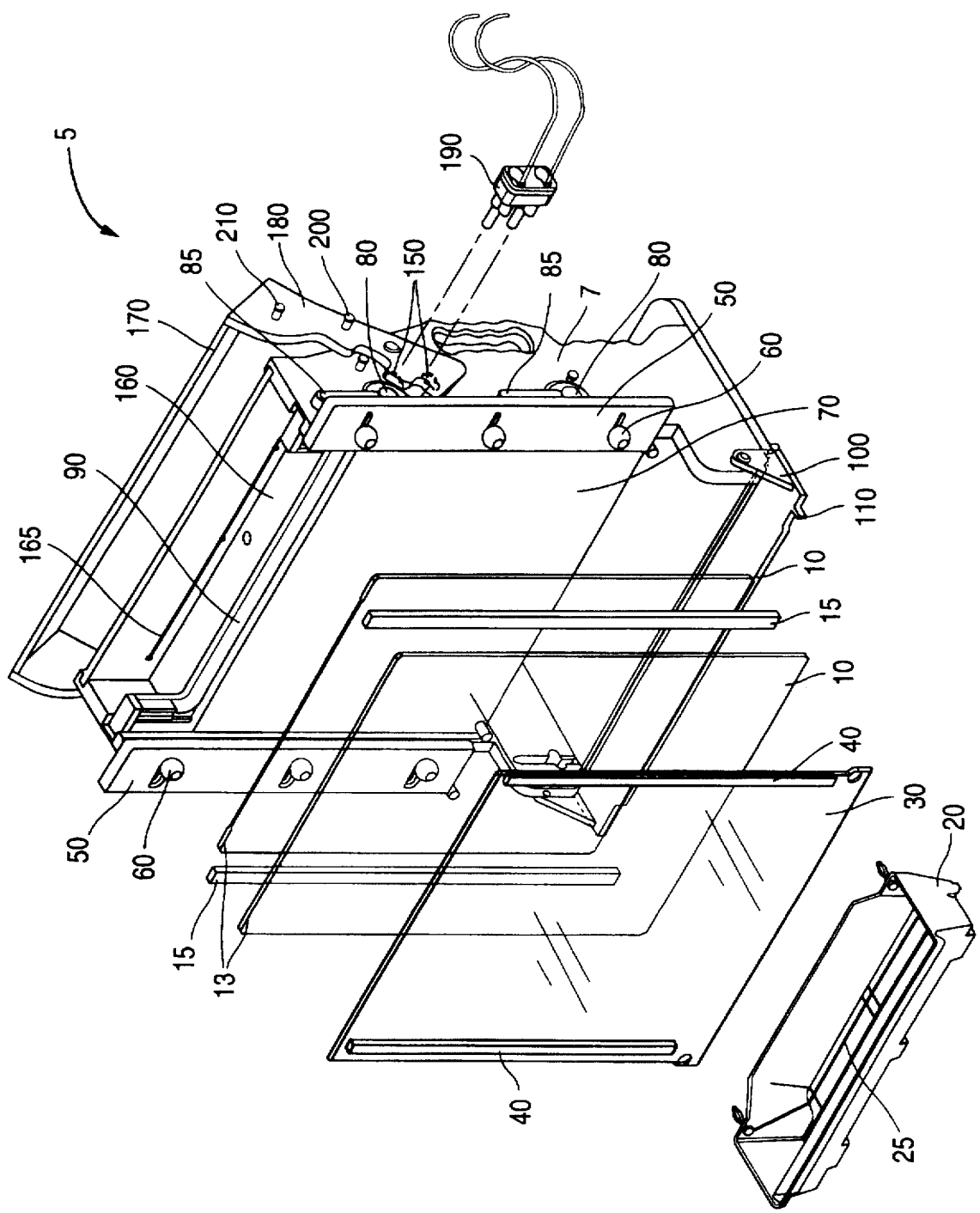
FIG. 1 shows a perspective top view of an exemplary embodiment of the invention.
Figure 2:
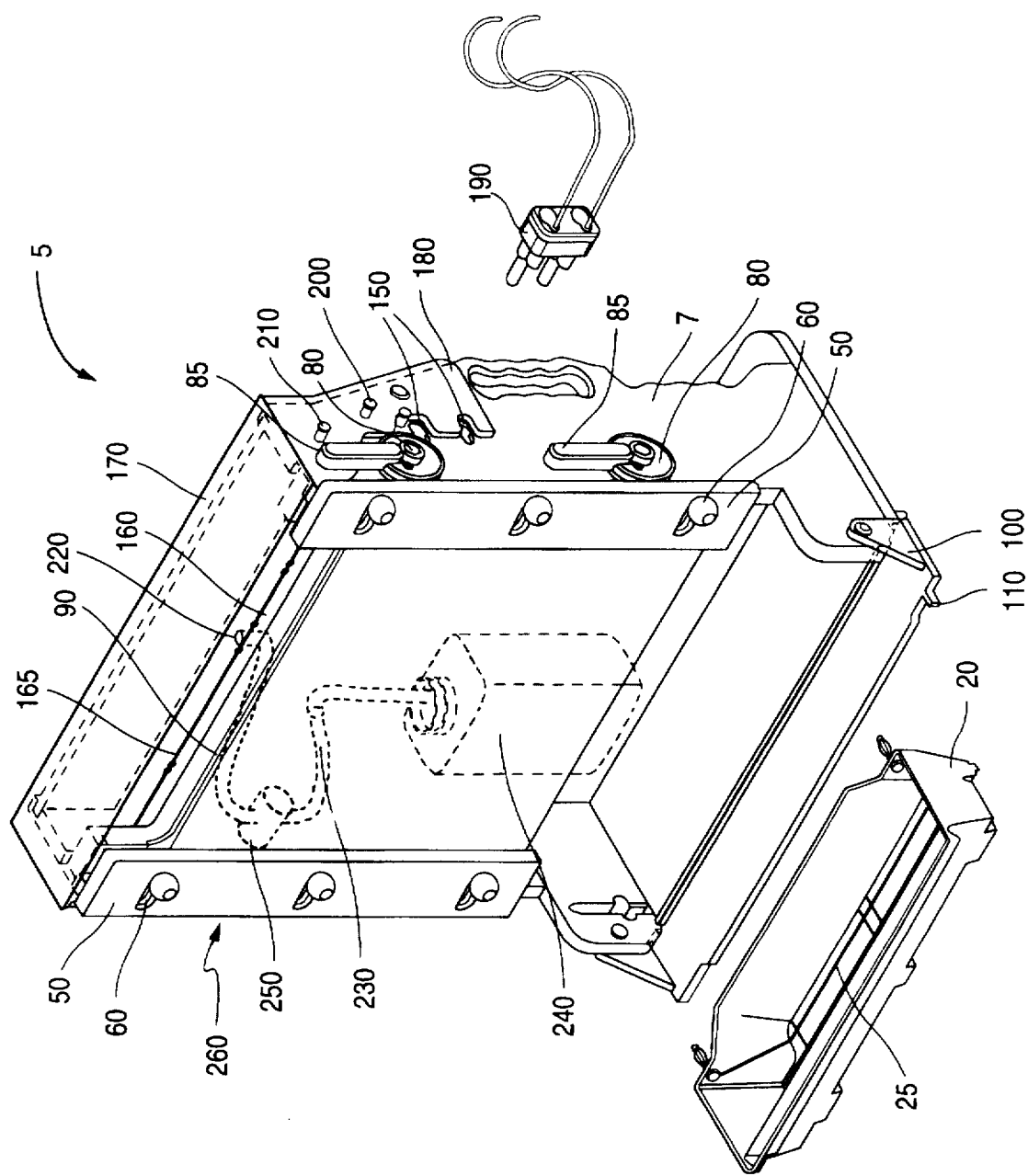
FIG. 2 shows a further perspective top view of the embodiment shown in FIG. 1.

FIGS. 1 and 2 show respectively an unassembled and partially assembled electrophoresis apparatus 5. Apparatus 5 includes side support frame members 7 for supporting other elements of the apparatus; a gel chamber 10 which is defined by front and back walls of plates 13. Chamber plates 13 are in turn, held apart by spacers 15. The apparatus further includes a lower buffer reservoir 20, in which lower electrode 25 is positioned. A protective screen 30 is positioned over one of plates 13 and includes spacers 40 attached down the vertical edges of the screen. Clamping bars 50 are mounted on frame members 7 via shoulder knobs 60.

A heat distribution plate 70 of the type commonly used is included, as are clamping cams 80 including clamping cam handles 85. An upper buffer gasket 90 is located adjacent upper buffer reservoir 160.

A lower buffer reservoir cover 100 (which includes an activation finger 110) forms part of the safety configuration of the invention. As will be explained in greater detail, the lower buffer reservoir cover 100 is "interlocked" with other elements to avoid shock hazard to the user.

As further shown in FIGS. 1 and 2, the apparatus further comprises power connector receptacle or sockets 150; an upper buffer reservoir 160 including upper electrode 165; an upper buffer reservoir cover 170 having a side extension 180. A power connector plug 190 is connected to a power source (not shown). Lower and upper blocking pins 200 and 210 are attached to the upper buffer reservoir cover side extension 180. An upper buffer reservoir drain opening 220 is connected to an upper buffer reservoir drain container 240 via drain tubing 230 and spring-loaded pinch clamp 250.

As is conventional, the gel itself will be formed between the glass plates and may be made of any suitable gel; for example, acrylamide. When the electrophoresis unit is assembled (FIG. 2), the gel chamber 10 is clamped in place against the heat distribution plate 70, which is conventionally made of aluminum.

In contrast to the conventional apparatus, the embodiment of the present invention shown in FIGS. 1 and 2 includes a protective screen 30, which is clamped in front of the exposed front surface of the gel chamber. The protective screen is for preventing an operator from contacting the hot gel chamber during operation of the electrophoresis unit or any electrically connected buffer in the event of leakage around or over the sealing gasket 90 or resulting from breakage of the glass walls 13 of the gel chamber 10. To accomplish this, the screen 30 should be large enough to completely cover the otherwise exposed surface of the chamber and is preferably made of a structurally rigid material such as glass or plastic. It is also preferred that the screen be made of an electrically and thermally insulating material and, in order that the operator may monitor the progress of the assay, it is preferred that the screen be made of a transparent material. Thus, the screen is preferably a rigid transparent plastic sheet. To further ensure the safety of the operator, the protective screen should be electrically and thermally insulated from the gel chamber. In the embodiment shown, this is achieved using spacers 40 (such as resilient foam strips) down the vertical edges of the protective screen.

In the embodiment shown in FIGS. 1 and 2, gel chamber 10 and protective screen 30 are clamped in place using clamping bars 50. In this arrangement, spacers 40, in addition to thermally and electrically insulating the protective screen from the chamber, also act to transmit pressure from clamping bars 50 to chamber 10. Clamping bars 50 are slidably restrained by shoulder knobs 60 which are also pivot points. When chamber 10 and protective screen 30 are in place against heat distribution plate 70, clamping bars 50 are slid to the "in" position, where they cover the edges of protective screen 30. The chamber and protective screen are clamped in place by turning clamping cams 80 approximately ¼ turn, which pivots clamping bar 50 on shoulder knobs 60 (FIGS. 1 and 2 show clamping cams 80 in their unclamped positions). Thus, the clamping bars apply pressure to protective screen 30, and thence through resilient foam strips 40 to gel assembly 10. This secures the protective screen and chamber in place and produces a liquid tight seal between chamber 10 and upper buffer gasket 90. To ensure that the chamber cannot be installed without the presence of the protective screen, the distance that clamping bars 50 pivot when clamping cams 80 are turned is insufficient to clamp the chamber 10 without the presence of protective screen 30.

As is conventional, the apparatus includes upper and lower buffer reservoirs, 160 and 20 respectively, for containing upper and lower buffer solutions. The upper and lower buffer reservoirs include upper and lower electrodes (typically platinum), 165 and 25 respectively, for contacting the buffer solutions to the power source. The upper and lower buffer reservoirs are protected by upper and lower buffer reservoir covers, 170 and 100 respectively.

Upper buffer reservoir cover 170 has two positions: an open position, shown in FIG. 1, in which it allows access to the upper buffer reservoir; and a closed position, shown in FIG. 2, in which it prevents operator access to the upper buffer reservoir. When upper buffer reservoir cover 170 is in the open position, the reservoir may be filled with buffer solution; on the other hand, when it is in its closed position, the operator cannot access the upper buffer reservoir and is therefore prevented from making contact with the upper buffer solution and the upper electrode. The lower buffer reservoir cover 100 also has two positions: an open position, shown in FIG. 3A, in which the lower buffer reservoir may be filled; and a closed position, shown in FIG. 3B, in which the operator is prevented from making contact with the lower buffer solution and the lower electrode.

To prepare the unit for operation, the operator fills lower buffer reservoir 20 with a sufficient volume of buffer solution to make liquid contact with the lower edge of the gel and fills the upper buffer reservoir with sufficient buffer solution to make liquid contact with the upper edge of the gel. The samples which are to be separated are placed close to the top edge of the gel and the upper and lower buffer solutions are then connected to the power supply via the upper and lower electrodes.

In contrast to the conventional apparatus, the present invention includes a power engaging mechanism that ensures that either both buffer solutions are connected to the power supply or neither buffer solution is connected to the power supply. The power engaging mechanism also ensures that both buffer solutions are connected to the power supply only when both buffer reservoir covers are in their closed positions and that both buffer reservoir covers are locked in their closed positions when the buffer solutions are connected to the power supply. With reference to FIGS. 1, 2, 3A and 3B a preferred form of the power engaging mechanism is described.

In the embodiment shown, the upper and lower electrodes are connected to the power supply by inserting power connector plug 190 into connector sockets 150. The power connector plug 190 contains power leads to both upper and lower electrodes in one integral unit. Therefore, when power connector plug 190 is inserted in connector sockets 150 both buffer solutions are connected to the power and when the plug is not inserted in the sockets neither buffer solution is connected to the power supply. This ensures that it is not possible to connect only one buffer solution to the power supply.

The power engaging mechanism is designed so that power connector plug 190 can only be inserted into connector sockets 150 when both reservoir covers are in their closed positions. For the upper reservoir cover, this is achieved using the position of the side extension 180 and for the lower reservoir cover, it is achieved using the position of a power connector shutter 140. This provides additional protection against users who might replace integral power connector plug 190 with individual power cords.

As shown in FIG. 1, when the upper buffer reservoir cover 170 is in its open position side, extensions 180 prevent plug 190 from being inserted into socket 150. On the other hand, FIG. 2 shows that when cover 170 is in its closed position, plug 190 can be inserted into socket 150. As can be seen from the geometry of side extension 180 in FIG. 2, when plug 1 90 is inserted into socket 150, side extension 180 is prevented from moving and upper buffer reservoir cover 170 is therefore locked in its closed position. The design of plug 190, sockets 1 50, and cover side extension 180 shown in FIGS. 1 and 2 therefore ensure that power can only be supplied to the buffer solutions when the upper cover 170 is closed and furthermore, that upper cover 170 is physically limited to its closed position when the power is connected.

FIGS. 3A and 3B show that the equivalent result for the lower buffer reservoir cover is achieved using power connector shutter 140 that is slidably attached to the frame. Shutter 140 includes openings 155 which are of the same size and arrangement as the sockets 150 in the frame and the shutter has two positions: a closed position (FIG. 3A) in which openings 155 in the shutter are not aligned with sockets 150 and an open position (FIG. 3B) in which openings 155 and sockets 150 are aligned. As can be seen from FIGS. 3A and 3B, power connector plug 190 can only be inserted into sockets 1 50 when they are aligned with the openings 155 in the shutter; that is, when the shutter is in its open position.

The position of shutter 140 is controlled by the position of the lower reservoir cover. If the lower reservoir cover 100 is in its open position, gravity (or a spring mechanism, not shown) ensures that the shutter is in its closed position—FIG. 3A. However, when the lower buffer reservoir cover is closed—FIG. 3B—an activation finger 110 presses down on shutter lever 120 which causes shutter 140 to be lifted into its open position. When the shutter is in this position, plug 190 can be inserted into aligned sockets 150 and openings 155 and the buffer solutions can be connected to the power supply. From FIG. 3B it can be seen that when plug 190 is inserted into aligned sockets 150 and openings 155 shutter 140 will be retained in its open position. The tip of shutter lever 120 is designed so that when shutter 140 is held open by the presence of plug 190, activation finger 110 is trapped, retaining cover 100 in its closed position. The arrangement of shutter 140, lower buffer reservoir cover 100, activation FIG. 110, shutter lever 120, openings 155, and sockets 150 shown in FIGS. 3A and 3B ensure that plug 190 can only be inserted into sockets 1 50 when lower reservoir cover 100 is in its closed position and that when plug 190 is inserted into sockets 150, cover 100 is locked in its closed position.

Figure 4:
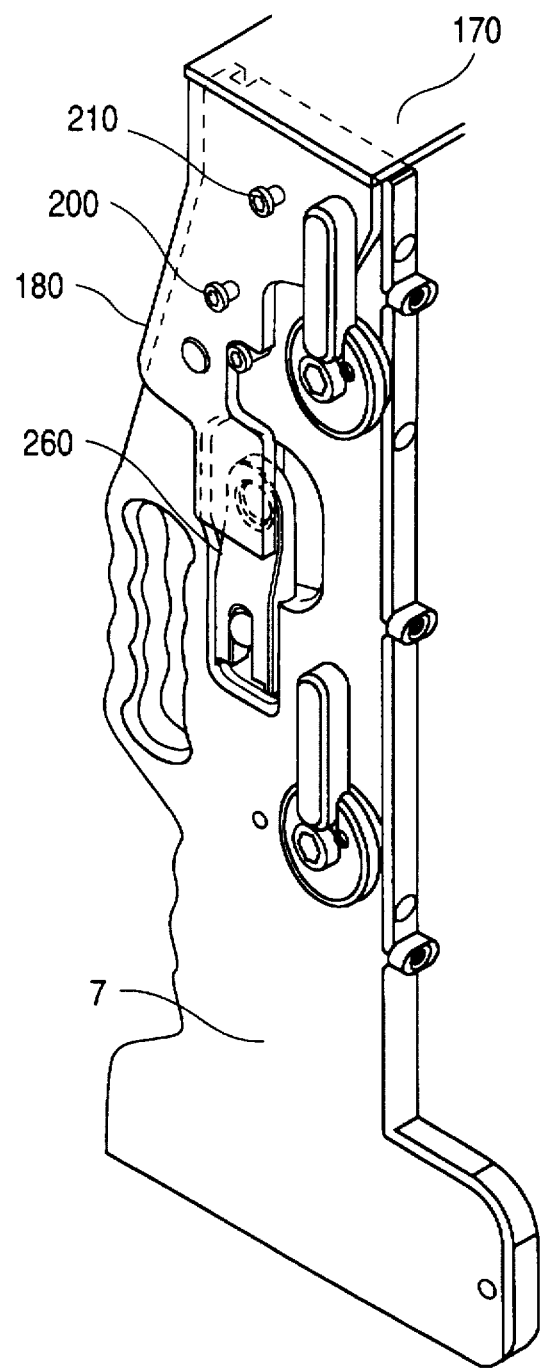
FIG. 4 shows a perspective top view of one aspect of the embodiment shown in FIGS. 1 and 2.

For easy draining of the upper buffer reservoir, the apparatus also includes an upper buffer reservoir drain container 240 which is connected to the upper buffer reservoir via drain tubing 230 and a drain opening 220. After operation of the unit, the upper buffer solution is drained into the drain container by opening the spring loaded pinch clamp 250 (FIG. 2). FIG. 4 shows one embodiment in which the pinch clamp is opened by pulling out a drain clamp handle 260. This embodiment includes a further safety feature that ensures that the upper buffer reservoir cannot be drained unless the power has been disconnected. FIG. 4 shows that when upper buffer reservoir cover 170 is in its closed position side extension 180 obstructs access to drain clamp handle 260. When the upper buffer reservoir cover is in its open position (not shown) the operator has access to the drain clamp handle. Since the reservoir cover can only be opened when the power is disconnected, the arrangement shown in FIG. 4 ensures that the upper buffer reservoir can only be drained when there is no power supplied to the unit.

The embodiment shown also includes the safety feature that when the chamber and protective screen are clamped to the frame they cannot be released while the unit is supplied with power. Since the clamped chamber retains the upper buffer solution in the upper buffer reservoir, this safety feature ensures that buffer solution cannot leak from the upper buffer reservoir while the apparatus is in use. FIGS. 1, 2, and 4 show an embodiment of the invention which includes this safety feature. In this embodiment, upper buffer reservoir cover side extensions 180 include lower blocking pins 200 which retain upper clamping cams 80 in their clamped position when the reservoir cover is in its closed position. Although not shown in the figures, when the clamping cams are in their clamped position, clamping cam handles 85 are horizontal and are pointing away from clamping bars 50. Therefore, it can be seen from FIG. 2 that the lower blocking pins 200 will prevent the upper clamping cams from being returned to their unclamped positions when the upper reservoir cover is closed. Since the upper reservoir cover is retained in its closed position when plug 190 is inserted in sockets 150, lower blocking pins 200 ensure that the upper clamping cams cannot be returned to their unclamped positions while the unit is supplied with power.

Though only a limited number of exemplary embodiments have been disclosed herein, those skilled in the art will nevertheless recognize many possible variations and modifications of the present invention which incorporate the key safety features disclosed. Applicants intend that variations which incorporate these safety features set forth in the appended claims shall be encompassed by the language thereof.

What is claimed is:

1. A gel electrophoresis apparatus comprising:

a gel chamber having an upper chamber opening and a lower chamber opening, and a front face;

first buffer reservoir adjacent to said upper chamber opening and including a first buffer fill opening and a first gel contact opening;

a second buffer reservoir adjacent to said lower chamber opening and including a second buffer fill opening and a second gel contact opening which is open to said lower chamber opening;

a power inlet receptacle;

electrodes positioned in said first and second reservoirs and in electrical contact with said power inlet receptacle;

first and second buffer fill opening covers, each having a cover open position and a cover closed position;

a first receptacle guard associated with said first buffer fill opening cover, said first receptacle guard blocking access to at least a portion of said receptacle when said first cover is in its cover open position; and a second receptacle guard, said second receptacle guard blocking access to at least a portion of said receptacle when said second cover is in its cover open position.

2. The gel electrophoresis apparatus of claim 1, said receptacle guard means further including means for retaining each of said first and second buffer fill opening covers in their cover closed position so long as a power supply plug is positioned in said receptacle.

3. The apparatus according to claim 1 further comprising a thermally and electrically insulating safety screen positioned over said front face of said chamber.

4. The apparatus according to claim 3 further comprising clamping means for releasably clamping said screen over said front face, including a clamping handle.

5. The apparatus according to claim 4 comprising screen retaining means for retaining said screen in position whenever said covers are in a closed position, said retaining means comprising a handle blocking pin positioned to prevent movement of said clamping handle from a screen clamped to a screen unclamped position.

6. The apparatus according to claim 1 further comprising a drain line connected to an opening in a bottom portion of said first buffer reservoir, and a drain line clamp, wherein said clamp is user accessible only when said covers are in their cover open positions.

7. A gel electrophoresis apparatus comprising:

a gel chamber having an upper chamber opening and a lower chamber opening;

a first buffer reservoir adjacent to said upper chamber opening and including a first buffer fill opening and a first gel contact opening;

a second buffer reservoir adjacent to said lower chamber opening and including a second buffer fill opening and a second gel contact opening which is open to said lower chamber opening;

a power inlet receptacle;

electrodes positioned in said first and second reservoirs and in electrical contact with said power inlet receptacle;

first and second buffer fill opening covers, each having a cover open position and a cover closed position;

receptacle guard means for blocking access to at least a portion of said receptacle when either one of said first or second covers is in its cover open position.

8. The gel electrophoresis apparatus of claim 7, said receptacle guard means further including means for retaining each of said first and second buffer fill opening covers in their cover closed position so long as a power supply plug is positioned in said receptacle.

9. An electrophoresis apparatus for use with a power source, the apparatus comprising:

(a) a chamber for containing a gel;

(b) a first buffer reservoir for containing a first buffer solution in contact with a first edge of the gel;

(c) a second buffer reservoir for containing a second buffer solution in contact with a second edge of the gel;

(d) a first cover for said first buffer reservoir;

(e) a second cover for said second buffer reservoir;

(f) means for connecting electrodes positioned in said buffer reservoirs to a power source including an electrical receptacle; and (g) receptacle guard means for blocking access to at least a portion of said electrical receptacle when either one of said first or second covers is in a cover open position.

10. The gel electrophoresis apparatus of claim 9, said receptacle guard means further including means for retaining each of said first and second buffer fill opening covers in their cover closed position so long as a power supply plug is positioned in said receptacle.

11. The apparatus according to claim 9 further including a safety screen positioned adjacent to said chamber and comprising clamping means for releasably clamping said screen over a face of said chamber, said clamping means including a clamping handle.

12. The apparatus according to claim 11 further comprising a clamping handle blocking pin positioned on said first reservoir cover to prevent movement of said clamping handle from a screen clamped to a screen unclamped position when said cover is in a closed position.

13. The apparatus according to claim 9 further comprising a drain line connected to an opening in a bottom portion of said first buffer reservoir, and a drain line clamp, wherein said clamp is user accessible only when said covers are in their cover open positions.

14. The apparatus according to claim 11, wherein the protective screen is transparent.

15. An electrophoresis apparatus for use with a power source, the apparatus comprising:

(a) a chamber for containing a gel;

(b) a first buffer reservoir for containing a first buffer solution in contact with a first edge of the gel;

(c) a second buffer reservoir for containing a second buffer solution in contact with a second edge of the gel;

(d) a protective screen composed of electrically and thermally insulating material for preventing an operator from contacting the chamber and covering at least one face of said chamber; and (e) insulating spacers positioned between said screen and said chamber and in contact with each.

16. The apparatus according to claim 15, further comprising clamping means for clamping the screen to the chamber.

17. The apparatus according to claim 16, wherein said clamping means further comprises means for releasing the protective screen from the chamber only when the buffer solutions are not connected to the power source.

18. The apparatus according to claim 15, further comprising reservoir draining means connected to the first buffer reservoir for draining the first buffer solution only when neither buffer solution is connected to the power source.

\* \* \* \* \*